United States Patent [19]

Lamberti et al.

[11] 4,060,495

[45] Nov. 29, 1977

[54] HYDROXYARYLDIALKYL SULFONIUM HALIDES

[75] Inventors: Vincent Lamberti, Upper Saddle River; Mark D. Konort, Haworth, both of N.J.

[73] Assignee: Lever Brothers Company, New York, N.Y.

[21] Appl. No.: 755,091

[22] Filed: Dec. 22, 1976

Related U.S. Application Data

[62] Division of Ser. No. 114,034, Feb. 9, 1971, Pat. No. 4,034,046.

[51] Int. Cl.[2] .................... A61L 13/00; C07C 149/46; C11D 3/48; C11D 9/50

[52] U.S. Cl. .................................... 252/106; 252/351; 252/530; 252/549; 260/607 B; 424/49; 424/335

[58] Field of Search ............... 252/106, 107, 530, 549, 252/351; 424/335, 49; 260/607 B

[56] References Cited

U.S. PATENT DOCUMENTS

| | | | |
|---|---|---|---|
| 2,121,823 | 6/1938 | Piggott | 424/335 X |
| 2,965,538 | 12/1960 | Weesner | 424/335 X |
| 3,133,971 | 5/1964 | MacGregor | 260/607 B |
| 3,259,660 | 5/1966 | Cisney | 260/607 B |
| 3,270,034 | 8/1966 | Greenbaum | 424/335 X |
| 3,944,498 | 3/1976 | Moyle | 252/106 |

*Primary Examiner*—Dennis L. Albrecht
*Attorney, Agent, or Firm*—Kenneth F. Dusyn; Michael J. Kelly; Melvin H. Kurtz

[57] ABSTRACT

Hydroxyaryldialkyl sulfonium halides having the structural formula

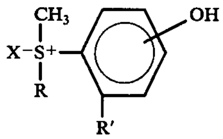

wherein R is a normal alkyl group having 10 to 20 carbon atoms, R' is hydrogen or methyl, and X is bromine or chlorine, provided that when R' is hydrogen, the hydroxyl group is in the ortho, meta or para position with respect to the sulfur atom, and provided that when R' is methyl, the hydroxyl group is in the para position with respect to the sulfur atom. The compounds are useful as germicidal agents, especially against gram positive bacteria, in germicidal compositions and in detergent formulations.

4 Claims, No Drawings

HYDROXYARYLDIALKYL SULFONIUM HALIDES

This is a division of application Ser. No. 114,034, filed Feb. 9, 1971, now U.S. Pat. No. 4,034,046.

SUMMARY OF THE INVENTION

It has been discovered that certain hydroxyaryldialkyl sulfonium halides have unusual germicidal activity, especially against gram positive bacteria.

The hydroxyaryldialkyl sulfonium halides of the invention have the structural formula

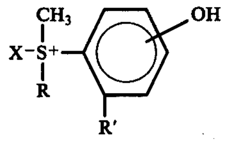

wherein R is a normal alkyl group having 10 to 20 carbon atoms, R' is hydrogen or methyl, and X is bromine or chlorine, provided that when R' is hydrogen, the hydroxyl group is in the ortho, meta or para position with respect to the sulfur atom, and provided that when R' is methyl, the hydroxyl group is in the para position with respect to the sulfur atom.

Accordingly one aspect of the invention is a germicidal composition containing such a hydroxyaryldialkyl sulfonium halide. A particular aspect of the invention is a germicidal detergent composition containing such a hydroxyaryldialkyl sulfonium halide. The germicidal detergent composition can be in any convenient form such as liquids, pastes, tablets, bars, granules or powders. Preferably the germicidal detergent compositions are non-ionic based formulations.

DETAILED DISCUSSION

The hydroxyaryldialkyl sulfonium halides of the invention are prepared generally according to the methods described in French Pat. No. 1,377,019, published Oct. 30, 1964, and French Pat. No. 1,348,846, published Jan. 10, 1964. An abstract of French Pat. No. 1,377,019 appears in Chemical Abstracts, Vol. 62, 7690d.

French Pat. No. 1,348,846 purports to describe the preparation of (4-hydroxyphenyl)-dioctyl sulfonium chloride by admixing dioctyl sulfide with hydroxybenzene in heptane and chlorinating the mixture while stirring with chlorine gas at a temperature of −10° to −15° C. French Pat. No. 1,348,846 purports to describe the preparation of (4-hydroxy-2methylphenyl)-dioctyl sulfonium chloride by chlorinating dioctyl sulfide admixed with heptane at −10° to −15° C and then adding cresol to the reaction mixture at low temperature.

The French patents describe the hydroxyaryldialkyl sulfonium chlorides as being useful as surfactants, biological poisons and material for organic synthesis.

The hydroxyaryldialkyl sulfonium chlorides of the present invention and corresponding to the structural formula given hereinbefore have been found to possess unusual germicidal activity, particularly against gram positive bacteria.

The preparation of the compounds of the present invention and of other compounds is described in the following examples.

EXAMPLE 1

A solution of 14 grams (0.1 mole) of 4-(methylthio)-phenol and 88.4 grams (0.4 mole) of n-decyl bromide in 70 ml. of absolute methanol was refluxed for 6 hours. The solvent was then evaporated in vacuo and the residue was treated with 200 ml. of absolute diethyl ether to precipitate the product. The white crystals which precipitated were filtered, dried and purified by dissolving them in a minimum amount of hot absolute methanol and reprecipitating with absolute ether. The product was filtered and dried to yield 3.2 grams of (4-hydroxyphenyl) n-decylmethyl sulfonium bromide. The structure of the product was confirmed by elemental analysis and infrared spectroscopy.

| | | |
|---|---|---|
| Analysis: | % S Theory: 8.9 | % Br Theory: 22.2 |
| | Found: 9.7 | Found: 20.9 |

EXAMPLE 2

The procedure of Example 1 was repeated except that 110.8 grams (0.4 mole) of n-tetradecyl bromide was employed, a mixture of 50 ml. ethanol and 70 ml. of methanol was used as the solvent, and the reaction time was 11 hours. The product was (4-hydroxyphenyl)n-tetradecylmethyl sulfonium bromide. The structure was confirmed by elemental analysis and infrared spectroscopy.

| | | |
|---|---|---|
| Analysis: | % S Theory: 7.7 | % Br Theory: 19.2 |
| | Found: 8.0 | Found: 19.5 |

EXAMPLE 3

The procedure of Example 1 was repeated except that 0.4 mole of n-pentyl bromide was employed and the reaction time was 9 hours. The product was (4-hydroxyphenyl)n-pentylmethyl sulfonium bromide.

| | | |
|---|---|---|
| Analysis: | % S Theory: 11.0 | % Br Theory: 27.5 |
| | Found: 11.3 | Found: 27.7 |

EXAMPLE 4

The procedure of Example 1 was repeated except that 0.4 mole of n-octyl bromide was employed and the reaction time was 4 hours. The product was (4-hydroxyphenyl)n-octylmethyl sulfonium bromide.

| | | |
|---|---|---|
| Analysis: | % S Theory: 9.7 | % Br Theory: 24.5 |
| | Found: 10.1 | Found: 23.9 |

EXAMPLE 5

The procedure of Example 1 was repeated except that 0.4 mole of n-dodecyl bromide was employed and the reaction time was 8 hours. The product was (4-hydroxyphenyl)n-dodecylmethyl sulfonium bromide.

| | | |
|---|---|---|
| Analysis: | % S Theory: 8.2 | % Br Theory: 20.6 |
| | Found: 7.6 | Found: 18.8 |

EXAMPLE 6

The procedure of Example 1 was repeated except that 0.4 mole of n-hexadecyl bromide was employed, 50 ml. of 3-A alcohol was added to the solvent, and the reaction time was 10 hours. The product was (4-hydroxyphenyl)n-hexadecylmethyl sulfonium bromide.

| | |
|---|---|
| Analysis: % S Theory: 7.2<br>Found: 7.6 | % Br Theory: 18.0<br>Found: 18.6 |

EXAMPLE 7

A solution of 266 grams (0.8 mole) of n-octadecyl bromide and 28 grams (0.2 mole) of 4-(methylthio)-phenol in 150 ml. of 3-A alcohol was refluxed for 30 hours. The solvent was then evaporated and the residue treated with absolute ether. The white crystals which precipitated were filtered, dried and purified by dissolving in a minimum amount of hot absolute methanol and precipitating with absolute ether. The product was filtered and dried to yield 2.3 grams of (4-hydroxyphenyl)n-octadecylmethyl sulfonium bromide.

| | |
|---|---|
| Analysis: % S Theory: 6.8<br>Found: 7.3 | % Br Theory: 16.9<br>Found: 16.9 |

EXAMPLE 8

The procedure of Example 1 was repeated except that 0.4 mole of 2,4-dichlorobenzyl chloride was employed instead of n-decyl bromide and the reaction time was 4 hours. The product was (4-hydroxyphenyl)2,4-dichlorobenzylmethyl sulfonium chloride.

| | |
|---|---|
| Analysis: % S Theory: 9.6<br>Found: 9.3 | % Cl Theory: 32.0<br>Found: 30.0 |

EXAMPLE 9

The procedures of Example 1, 2, 4, 5, 6 and 8 were repeated except that 0.1 mole of 4-(methylthio)-m-cresol was employed instead of 4-(methylthio)phenol. The corresponding products and the reaction and analytical data were as follows:

9a (2-methyl-4-hydroxyphenyl)n-decylmethyl sulfonium bromide
Solvent: 80 ml. absolute methanol
Reaction Time: 11 hours Analysis: % S Theory: 8.5
Found: 8.4

9b (2-methyl-4-hydroxyphenyl)n-tetradecylmethyl sulfonium bromide
Solvent: 50 ml. methanol and 25 ml. ethanol
Reaction Time: 16 hours Analysis: % S Theory: 7.4
Found: 7.1

9c (2-methyl-4-hydroxyphenyl)n-octylmethyl sulfonium bromide
Solvent: 80 ml. absolute methanol
Reaction Time: 11 hours

| | |
|---|---|
| Analysis: % S Theory: 9.2<br>Found: 9.3 | % Br Theory: 23.1<br>Found 23.0 |

9d (2-methyl-4-hydroxyphenyl)n-dodecylmethyl sulfonium bromide
Solvent: 80 ml. absolute methanol
Reaction Time: 10 hours

| | |
|---|---|
| Analysis: % S Theory: 7.9<br>Found: 8.0 | % Br Theory: 19.9<br>Found: 19.8 |

-continued

9e (2-methyl-4-hydroxyphenyl)n-hexadecylmethyl sulfonium bromide
Solvent: 50 ml. methanol and 50 ml. ethanol
Reaction Time: 15 hours Analysis: % S Theory: 7.0
Found: 6.2

9f (2-methyl-4-hydroxyphenyl)-2,4-dichlorobenzylmethyl sulfonium chloride

Analysis: % S Theory: 9.2
Found: 9.9

EXAMPLE 10

The procedure of Example 1 was repeated except that 2-(methylthio)-phenol was employed and the reaction time was 14 hours. The product was (2-hydroxyphenyl)n-dodecylmethyl sulfonium bromide.

| | |
|---|---|
| Analysis: % S Theory: 8.2<br>Found: 9.0 | % Cl Theory: 20.6<br>Found: 21.6 |

EXAMPLE 11

The procedure of Example 1 was repeated except that benzyl chloride was employed instead of n-dodecyl bromide and 4-(methylthio)-m-cresol was employed instead of 4-(methylthio)phenol. The product was (2-methyl-4-hydroxyphenyl)benzylmethyl sulfonium chloride.

| | |
|---|---|
| Analysis: % S Theory: 11.4<br>Found: 10.9 | % Cl Theory: 12.6<br>Found: 10.8 |

It was found that straight chain chlorides were not reactive enough to form the corresponding sulfonium chlorides according to the procedure of Example 1 even at elevated temperatures and under pressure.

EXAMPLE 12

(4-hydroxyphenyl)n-tetradecylmethyl sulfonium chloride was prepared using as reactants n-tetradecylmethyl sulfide, chlorine and phenol according to the general procedure described in French Pat. No. 1,377,019. The product has a melting point of 136.2° - 137.2° C. and the structure was confirmed by elemental and NMR analyses.

The unique germicidal properties of the products within the scope of this invention are shown in the following Table I in comparison with other products.

The data in Table I show that the germicidal activity of the compounds within the scope of the invention, i.e. the compounds of Examples 1, 2, 5, 6, 7, 9a, 9b, 9d, 9e, 10 and 12, is of a different order of magnitude than the activity of the compounds without the scope of the invention, i.e. Examples 3, 4, 8, 9c, 9f and 11.

In Table I, the germicidal (antimicrobial) activity of the compounds was determined by the Streak Gradient Plate Method. The Streak Gradient Plate Method is a modification of the gradient plate method of Szybalski, *Science* 116: 46-48 (1952), for the determination of germicide Mec (Minimum Effective Concentration) values. This method employs streaks of several organisms per plate.

The cultures employed and identified in Table I were as follows:

| | | | |
|---|---|---|---|
| Sa | - *Staphylococcus aureus* | | |
| Js | - Skin *staphylococcus* isolate | | |
| Ba | - *Brevibacterium ammoniagenes* | Gram Positive Organisms | |
| Se | - *Staphylococcus epidermidis* | | |
| Sf | - *Streptococcus faecalis* | | |
| E | - *Enterobacter aerogenes* | | |
| Ec | - *Escherichia coli* | | |
| Sc | - *Salmonella choleraesuis* | Gram Negative Organisms | |
| Ps | - *Pseudomonas aeruginosa* | | |
| Po | - *Pityosporum ovale* | - | yeast |
| Ca | - *Candida albicans* | - | yeast |
| An | - *Aspergillus niger* | - | mold |
| #85 | - Mildew isolate (unidentified) | - | mold |

TABLE I

| | Germidical Activity MEC By The Gradient Plate Method | | | | | | | | | | | | |
|---|---|---|---|---|---|---|---|---|---|---|---|---|---|
| | Test Organisms | | | | | | | | | | | | |
| Example | Sa | Js | Ba | Se | Sf | E | Ec | Sc | Ps | Po | Ca | An | #85 |
| 1 | 5.6 | 4.4 | 16 | 5.0 | 56 | 140 | 170 | 160 | — | 31 | 130 | 5.6 | — |
| 2 | 1.6 | 1.0 | 2.8 | 0.56 | 4.9 | 310 | 500 | 560 | — | 2.9 | 22 | 3.6 | — |
| 3 | 430 | 430 | 333 | 360 | 450 | 500 | — | — | — | 320 | 500 | 500 | — |
| 4 | 50 | 50 | 140 | 37 | 240 | 320 | 300 | 310 | 220 | 42 | 170 | — | 110 |
| 5 | 1.6 | 1.0 | 3.6 | 1.0 | 12 | 100 | 320 | 310 | — | 2.5 | 25 | 11 | — |
| 6 | 2.2 | 1.4 | 2.8 | 1.0 | 5.6 | 360 | >1000 | → | — | 10 | 22 | 11 | — |
| 7 | 2.2 | 2.5 | 50. | 5.0 | 10 | >1000 | → | → | 500 | 17 | 100 | — | 17 |
| 8 | 110 | 59 | 210 | 42 | 340 | 220 | 240 | 180 | 220 | 110 | 150 | — | 170 |
| 9c | 6.1 | 14 | 50 | 17 | 210 | 440 | 300 | 360 | 560 | 110 | 180 | — | 120 |
| 9a | 2.5 | 2.2 | 13 | 2.2 | 29 | 100 | 170 | 140 | — | 14 | 62 | 40 | — |
| 9d | 1.4 | 0.29 | 2.2 | 0.64 | 4.4 | 100 | 290 | 340 | 500 | 2.2 | 21 | — | 3.5 |
| 9b | 1.4 | 1.0 | 2.0 | 1.0 | 4.9 | 290 | 340 | 360 | — | 5.6 | 26 | 5.0 | — |
| 9e | 2.9 | 2.2 | 2.2 | 1.1 | 10 | 290 | 420 | 330 | — | 10 | 100 | 17 | — |
| 9f | 56 | 28 | 150 | 23 | 280 | 330 | 440 | 390 | 370 | 120 | 260 | — | 170 |
| 10 | 5.0 | 5.6 | 4.0 | 4.0 | 18 | >1000 | → | → | → | 18 | 22 | — | 22 |
| 11 | 150 | 150 | 240 | 67 | 440 | 260 | 280 | 220 | 230 | 170 | 250 | — | 220 |
| 12 | 1.1 | 0.41 | 1.6 | 1.0 | 1.8 | 330 | 380 | 1000 | — | 1.9 | — | — | 2.2 |

The following examples illustrate detergent formulations which are germicidal detergent compositions of the invention. In sanitizing cleaners, for example, those used for hospital linen, the hydroxyaryldialkyl sulfonium halides exhibit fabric substantivity in addition to germicidal activity. Also in the rinse compositions, the hydroxyaryldialkyl sulfonium halides having 16–20 carbon atoms in an alkyl group act as fabric softeners in addition to imparting germicidal activity.

In the germicidal detergent compositions, the germicidally effective amount of the hydroxyaryldialkyl sulfonium halide is generally within the range of about 0.1 to 5.0, preferably 0.5 to 2.0 percent by weight of the total composition.

EXAMPLE 13

A formulation for a germicidal detergent composition in powder form is as follows in parts by weight:

40% TPP (Sodium tripolyphosphate)
10% Neodol-45-11*
6% Sodium silicate ($SiO_2$:$Na_2O$, 2.4)
26% Sodium sulfate
15% Water
1% Carboxymethyl cellulose
1% Product of Example 2
1% Miscellaneous (including perfume, colorants, fluorescent dyes, etc.)

*Neodol-45-11 is an oxyethylated $C_{14}$–$C_{15}$ primary alcohol having 11 ethoxy groups per mole.

EXAMPLE 14

A formulation for a germicidal composition in liquid form having fabric softening characteristics is as follows in parts by weight:

2% Product of Example 5
4% Product of Example 7
92% Water
0.5% Neodol-45-11
1.5% Miscellaneous (including perfume, colorants, fluorescent dyes, etc.)

EXAMPLE 15

Another formulation for a germicidal composition in liquid form is as follows in parts by weight:

3% Arquad-2-HT*
2% Product of Example 5
90% Water
0.5% Tergitol-15-S-7**
4.5% Perfume, coloring, filler, etc.

*Arquad-2-HT is di(hydrogenated tallow) dimethyl ammonium chloride
**Tergitol-15-S-7 is an oxyethylated $C_{11}$–$C_{15}$ secondary alcohol having 7 ethoxy groups per mole.

EXAMPLE 16

A germicidal composition for oral cleaning (i.e. a mouthwash) is as follows:

0.1% Product of Example 5
0.03% Saccharin
0.3Flavor
5.0% Glycerin
18.0% Ethanol
balance to 100% (including water, colorant, etc.)

, We claim:

1. A germicidal detergent composition containing a germicidally effective amount of (4-hydroxyphenyl)n-dodecylmethyl sulfonium bromide or chloride.

2. A germicidal detergent composition containing a germicidally effective amount of (4-hydroxyphenyl)n-tetradecylmethyl sulfonium bromide or chloride.

3. A germicidal detergent composition containing a germicidally effective amount of (2-methyl-4-hydroxyphenyl) n-dodecylmethyl sulfonium bromide or chloride.

4. A germicidal detergent composition containing a germicidally effective amount of (2methyl-4-hydroxyphenyl) n-tetradecylmethyl sulfonium bromide or chloride.

* * * * *